US007843194B2

(12) United States Patent
Kassai

(10) Patent No.: US 7,843,194 B2
(45) Date of Patent: Nov. 30, 2010

(54) MAGNETIC RESONANCE IMAGING APPARATUS AND MAGNETIC RESONANCE IMAGING METHOD

(75) Inventor: Yoshimori Kassai, Nasushiobara (JP)

(73) Assignees: Kabushiki Kaisha Toshiba, Minato-Ku, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 106 days.

(21) Appl. No.: 12/389,700

(22) Filed: Feb. 20, 2009

(65) Prior Publication Data

US 2009/0174405 A1 Jul. 9, 2009

Related U.S. Application Data

(63) Continuation-in-part of application No. PCT/JP2008/072179, filed on Dec. 5, 2008.

(30) Foreign Application Priority Data

Dec. 6, 2007 (JP) ............................ 2007-316060

(51) Int. Cl.
*G01V 3/00* (2006.01)

(52) U.S. Cl. ...................................... 324/309; 324/307

(58) Field of Classification Search ................. 324/309, 324/307
See application file for complete search history.

(56) References Cited

U.S. PATENT DOCUMENTS 4,700,136 A * 10/1987 Yamaguchi et al. ......... 324/309
6,144,202 A * 11/2000 Kanazawa et al. .......... 324/309
6,479,999 B1 * 11/2002 DeMeester et al. .......... 324/318
6,700,373 B2 * 3/2004 Mueller et al. .............. 324/309

FOREIGN PATENT DOCUMENTS

| | | |
|---|---|---|
| JP | 3-118707 | 12/1991 |
| JP | 5-137707 | 6/1993 |
| JP | 6-86770 | 3/1994 |
| JP | 2007-325665 | 12/2007 |
| WO | 2009/072619 | 6/2009 |

OTHER PUBLICATIONS

Japanese-language International Search Report for PCT/JP2008/072179, mailed Jan. 6, 2009.

Notice of publication of WO 2009/072619, (Jun. 2009).

International Search Report mailed Jan. 6, 2009 in PCT/JP2008/072179.

* cited by examiner

*Primary Examiner*—Louis M Arana
(74) *Attorney, Agent, or Firm*—Nixon & Vanderhye PC

(57) ABSTRACT

A magnetic resonance imaging apparatus includes a generation unit configured to generate a magnetic field, a reconstruction unit configured to reconstruct an image for a subject on the basis of a magnetic resonance signal radiated from the subject in the magnetic field, a presumption unit configured to presume a distribution of an image quality deterioration degree occurring in the image on the basis of a precision at which the generation unit generates the magnetic field, and a creation unit configured to create a display image showing the distribution of the image quality deterioration degree on the image.

18 Claims, 12 Drawing Sheets

START
POSITIONING IMAGING — Sa1
DETERMINE INAPPROPRIATE REGION — Sb1
DECIDE POSITIONING IMAGE — Sb2
DECIDE IMAGING REGION — Sa4
IS INAPPROPRIATE REGION INCLUDED? — Sb3
No
Yes
ALARM DISPLAY — Sb4
IS IMAGING REGION CHANGED? — Sb5
Yes
SET CHANGED IMAGING REGION — Sb6
No
PRESENT IMAGING — Sa5
END 100
10
10a
INTERFACE PART
10b
DATA COLLECTING PART
10c
RECONSTRUCTION PART
10d
STORAGE PART
10e
DISPLAY PART
10f
INPUT PART
10g
MAIN CONTROL PART
3
GRADIENT MAGNETIC FIELD POWER SOURCE
9
RECEIVING UNIT
7
SENDING UNIT
5
BED CONTROL UNIT
1
2
6
8
200
4
41

FIG. 2

| COORDINATE | | | DEVIATION AMOUNT |
|---|---|---|---|
| X | Y | Z | |
| 0 | 0 | 0 | 0mm |
| ⋮ | | | ⋮ |
| 32 | | | 5mm |
| ⋮ | ⋮ | | ⋮ |
| 0 | 32 | | 0mm |
| ⋮ | | | ⋮ |
| 32 | | | 15mm |
| 0 | 0 | 1 | 0mm |
| ⋮ | ⋮ | | ⋮ |
| 0 | 32 | | 5mm |
| ⋮ | ⋮ | | ⋮ |
| 32 | 32 | | 15mm |
| ⋮ | ⋮ | ⋮ | ⋮ |
| 32 | 32 | 32 | 30mm |

FIG. 3

| COORDINATE | | | DEVIATION AMOUNT |
|---|---|---|---|
| X | Y | Z | |
| 0 | 0 | 0 | 0ppm |
| ⋮ | | | ⋮ |
| 32 | | | 3ppm |
| ⋮ | ⋮ | | ⋮ |
| 0 | 32 | | 3ppm |
| ⋮ | | | ⋮ |
| 32 | | | 10ppm |
| 0 | 0 | 1 | 0ppm |
| ⋮ | ⋮ | | ⋮ |
| 0 | 32 | | 3ppm |
| ⋮ | ⋮ | | ⋮ |
| 32 | 32 | | 10ppm |
| ⋮ | ⋮ | ⋮ | ⋮ |
| 32 | 32 | 32 | 20ppm |

*FIG. 4*

| COORDINATE | | | DEVIATION AMOUNT |
|---|---|---|---|
| X | Y | Z | |
| 0 | 0 | 0 | 100% |
| ⋮ | | | ⋮ |
| 32 | | | 70% |
| ⋮ | ⋮ | | ⋮ |
| 0 | 32 | | 70% |
| ⋮ | | | ⋮ |
| 32 | | | 50% |
| 0 | 0 | 1 | 100% |
| ⋮ | ⋮ | | ⋮ |
| 0 | 32 | | 70% |
| ⋮ | ⋮ | | ⋮ |
| 32 | 32 | | 50% |
| ⋮ | ⋮ | ⋮ | ⋮ |
| 32 | 32 | 32 | 20% |

START
POSITIONING IMAGING
Sa1
DETERMINE INAPPROPRIATE REGION
Sb1
DECIDE POSITIONING IMAGE
Sb2
DECIDE IMAGING REGION
Sa4
IS INAPPROPRIATE REGION INCLUDED?
Sb3
No
Yes
ALARM DISPLAY
Sb4
IS IMAGING REGION CHANGED?
Sb5
Yes
No
SET CHANGED IMAGING REGION
Sb6
PRESENT IMAGING
Sa5
END

MAGNETIC RESONANCE IMAGING APPARATUS AND MAGNETIC RESONANCE IMAGING METHOD

CROSS REFERENCE TO RELATED APPLICATIONS

This is a Continuation-In-Part Application of PCT Application No. PCT/JP2008/072179 (designating the United States), filed Dec. 5, 2008, which was published under PCT Article 21(2) in Japanese.

This application is based upon and claims the benefit of priority from prior Japanese Patent Application No. 2007-316060, filed Dec. 6, 2007, the entire contents of which are incorporated herein by reference.

BACKGROUND OF THE INVENTION

1. Field of the Invention

The present invention relates to a magnetic resonance imaging apparatus, obtaining an image for a subject on the basis of a magnetic resonance signal radiated from the subject in a magnetic field, and a magnetic resonance imaging method.

2. Description of the Related Art

In a magnetic resonance imaging (MRI), a spatial linearity of a gradient magnetic field is a very important factor to allow a spatial position relationship of a subject to be realized in an image. In a general electromagnetic solution, a model having an unlimited length may be supposed. However, in a spatial range of a static magnetic field, a gradient magnetic field, and an RF excitation magnetic field in actual, the length is limited due to an effective field of view for imaging a human body. For this reason, a linearity of the gradient magnetic field or a spatial uniformity of the static magnetic field or the RF excitation magnetic field deteriorates at a peripheral portion of each magnetic field irrespective of a center portion of each magnetic field.

As described above, there is a certain limitation in the spatial linearity of the gradient magnetic field or the spatial uniformity of the static magnetic field and the RF excitation magnetic field as long as the imaging is carried out within the limited length. In the related art, the efficient field of view (efficient FOV) is expressed in combination of the magnetic fields. Then, in terms of a manual or an operator instruction, it is emphasized that it is desirable to carry out the imaging within about 50 cm or to carry out the imaging at a position closest to a center of a magnet to obtain an image having an excellent image quality.

For this reason, in general, an operator who wants to reliably obtain a satisfactory image sets a small imaging region so that an imaging region is reliably included in the efficient FOV. That is, since the imaging uses only a part of a region capable of carrying out the satisfactory imaging in actual, efficiency is poor. In the case where the operator sets the large imaging region by predicting that the satisfactory imaging is carried out in a region larger than the efficient FOV, the imaging region may not be included in the region capable of carrying out the satisfactory imaging in actual. As a result, in this case, the image quality deteriorates.

In recent years, in order to reduce a subject' psychological pressure, a decrease in size is realized in a direction of a gantry bed. Thus, a spatial uniformity of the static magnetic field and the RF excitation magnetic field deteriorates. Additionally, a high SR (slew rate) is required in a sequence of an EPI (echo planar imaging) or an SSFP (steady state free precession) system. Additionally, it is required to reduce a magnetic stimulation derived from dB/dt (magnetic-field-strength time variation rate) generated by a switching of the gradient magnetic field. In order to satisfy both requirements, a gradient magnetic field coil is often designed in a nonlinear shape, and a spatial linearity of the gradient magnetic field tends to gradually deteriorate. Further, the magnetic stimulation indicates that current in accordance with a variation in magnetic flux at an initial rise of the gradient magnetic field generated by the switching of the gradient magnetic field is formed in a pulse shape and flows to a nerve to occur paralysis.

PATENT DOCUMENT 1: Japanese Patent Application Laid-Open No. 5-137707

BRIEF SUMMARY OF THE INVENTION

Likewise, since the region capable of carrying out the satisfactory imaging is limited, it is important to efficiently use the region for the efficient imaging, but it is difficult to appropriately set the imaging region.

The present invention is contrived in consideration of the above-described problems, and an object of the invention is to prevent a region where image quality deteriorates due to an influence of a magnetic field front being erroneously set to an imaging region.

According to a first aspect of the invention, there is disclosed a magnetic resonance imaging apparatus including: a generation unit configured to generate a magnetic field; a reconstruction unit configured to reconstruct an image for a subject on the basis of a magnetic resonance signal radiated from the subject in the magnetic field; a presumption unit configured to presume a distribution of an image quality deterioration degree occurring in the image on the basis of a precision at which the generation unit generates the magnetic field; and a creation unit configured to create a display image showing the distribution of the image quality deterioration degree on the image.

According to a second aspect of the invention, there is disclosed a magnetic resonance imaging apparatus including: a generation unit configured to generate a magnetic field; a presumption unit configured to presume a distribution of an image quality deterioration degree occurring in an image on the basis of a precision at which the generation unit generates the magnetic field; a determination unit configured to determine an inappropriate region having an image quality deterioration of which a degree exceeds an allowable level on the basis of the distribution of the image quality deterioration degree; a setting unit configured to set an imaging region, which is a target for reconstructing a medical diagnostic image for a subject, in accordance with an operator's instruction; an information unit configured to inform the operator of a fact that the imaging region includes the inappropriate region; and a reconstruction unit configured to reconstruct an image for the subject on the imaging region on the basis of a magnetic resonance signal radiated from the subject in the magnetic field.

According to a third aspect of the invention, there is disclosed a magnetic resonance imaging method including the steps of: generating a magnetic field; presuming a distribution of an image quality deterioration degree occurring in an image on the basis of a precision at which the generation unit generates the magnetic field; determining an inappropriate region having an image quality deterioration of which a degree exceeds an allowable level on the basis of the distribution of the image quality deterioration degree; setting an imaging region, which is a target for reconstructing a medical diagnostic image for a subject, in accordance with an operator's instruction; informing the operator of a fact that the imaging region includes the inappropriate region; and reconstructing an image for the subject on the imaging region on the basis of a magnetic resonance signal radiated from the subject in the magnetic field.

BRIEF DESCRIPTION OF THE SEVERAL VIEWS OF THE DRAWING

FIG. 2 is a diagram showing an example of a gradient magnetic field map.

FIG. 3 is a diagram showing an example of a static magnetic field map.

FIG. 4 is a diagram showing an example of an RF magnetic field map.

DETAILED DESCRIPTION OF THE INVENTION

Hereinafter, exemplary embodiments of the invention will be described with reference to the accompanying drawings.

Figure 1:
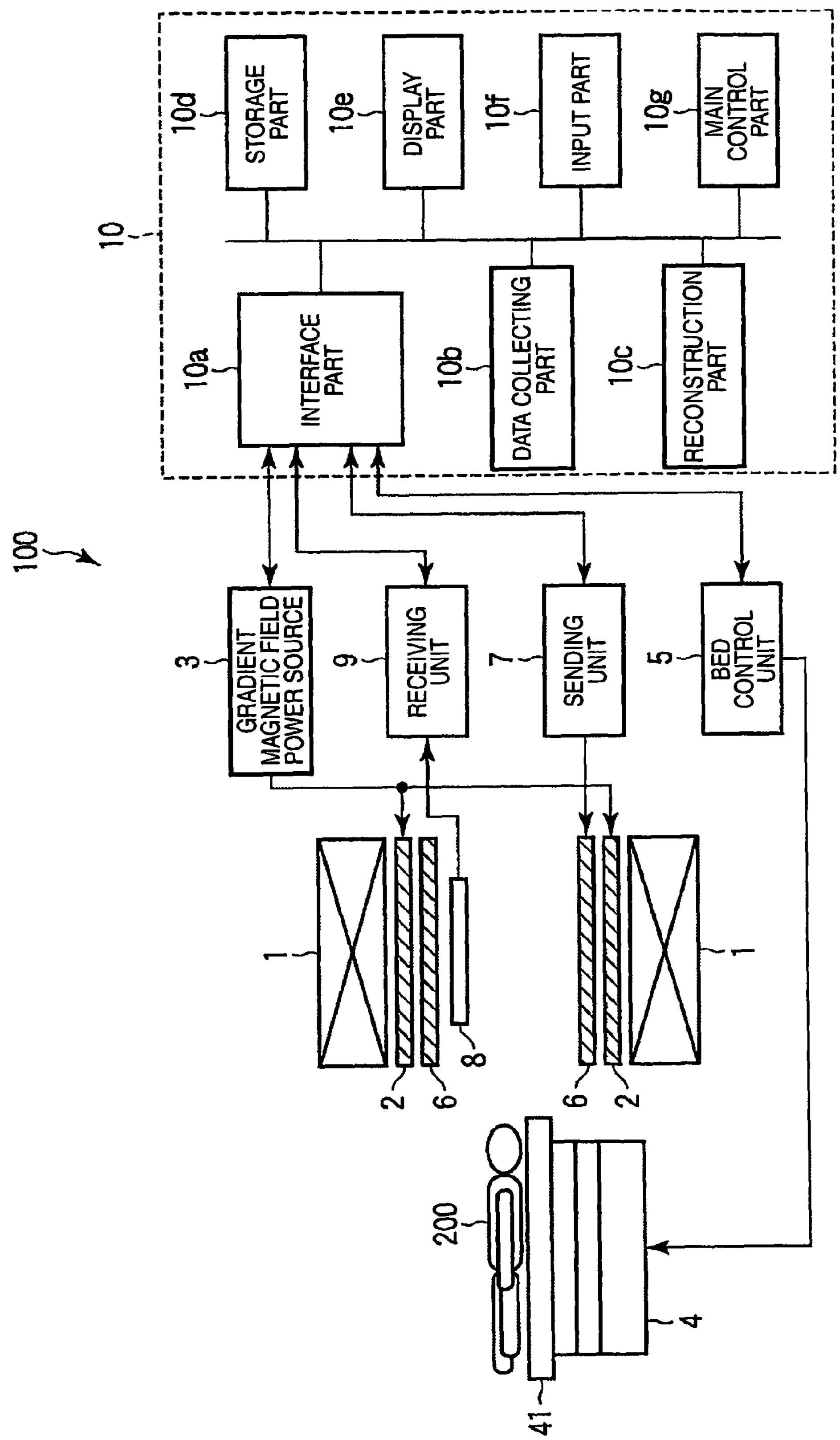
FIG. 1 is a diagram showing a configuration of a magnetic resonance imaging apparatus (MRI apparatus) according to an embodiment of the invention.

FIG. 1 is a diagram showing a configuration of a magnetic resonance imaging apparatus (MRI apparatus) 100 according to an embodiment. The MRI apparatus 100 includes a static magnetic field magnet 1, a gradient magnetic field coil 2, a gradient magnetic field power source 3, a bed 4, a bed control unit 5, a sending RF coil 6, a sending unit 7, a receiving RF coil 8, a receiving unit 9, and a computer system 10.

The static magnetic field magnet 1 is formed into a hollow cylindrical shape, and generates a uniform static magnetic field in its inner space. As the static magnetic field magnet 1, for example, a permanent magnet, a superconductive magnet, or the like is used.

The gradient magnetic field coil 2 is formed in a hollow cylindrical shape, and is disposed on the inside of the static magnetic field magnet L. The gradient magnetic field coil 2 is configured in such a manner that three types of coils corresponding to X, Y, and Z axes which intersect each other are combined. The gradient magnetic field coil 2 generates a gradient magnetic field of which a magnetic field strength is changed along the X, Y, and Z axes at the time when the gradient magnetic field power source 3 supplies current to each of the three types of coils. Additionally, the Z-axis direction is set to the same direction as that of, for example, the static magnetic field. The gradient magnetic fields in the X, Y, and Z axes, for example, correspond to a slice selecting gradient magnetic field Gs, a phase encoding gradient magnetic field Ge, and a readout gradient magnetic field Gr, respectively. The slice selecting gradient magnetic field Gs is used to arbitrarily decide an imaging section. The phase encoding gradient magnetic field Ge is used to change a phase of a magnetic resonance signal in accordance with a spatial position. The readout gradient magnetic field Gr is used to change a frequency of the magnetic resonance signal in accordance with the spatial position.

A subject 200 is allowed to enter a hollow (imaging space) of the gradient magnetic field coil 2 while being placed on a top plate 41 of the bed 4. The top plate 41 of the bed 4 is driven by the bed control unit 5 so as to move in longitudinal and vertical directions. In general, the bed 4 is installed so that a central axis of the static magnetic field magnet 1 is in parallel to a longitudinal direction.

The sending RF coil 6 is disposed on the inside of the gradient magnetic field coil 2. The sending RF coil 6 receives a high-frequency pulse from the sending unit 7 and generates a high-frequency magnetic field (RF magnetic field). As the sending RF coil 6, for example, a body (WB) coil is used.

The sending unit 7 sends a high-frequency pulse corresponding to a Larmor frequency to the sending RF coil 6.

The receiving RF coil 8 is disposed on the inside of the gradient magnetic field coil 2. The receiving RF coil 8 receives a magnetic resonance signal radiated from the subject due to the influence of the RF magnetic field. An output signal of the receiving RF coil 8 is input to the receiving unit 9.

The receiving unit 9 creates a magnetic resonance signal data on the basis of the output signal obtained from the receiving RF coil 8.

The computer system 10 includes an interface part 10*a*, a data collecting part 10*b*, a reconstruction part 10*c*, a storage part 10*d*, a display part 10*e*, an input part 10*f*, and a main control part 10*g*.

The interface part 10*a* is connected to the gradient magnetic field power source 3, the bed control unit 5, the sending unit 7, the receiving RF coil 8, the receiving unit 9, and the like. The interface part 10*a* is used to input and output signals sent and received between the respective connected units and the computer system 10.

The data collecting part 10*b* collects a digital signal output from the receiving unit 9 via the interface part 10*a*. The data collecting part 101 stores the collected digital signal, that is, the magnetic resonance signal data in the storage part 10*d*.

The reconstruction part 10*c* performs a post-process, that is, a reconstruction such as a Fourier transform on the magnetic resonance signal data stored in the storage part 10*d*, and obtains a spectrum data or an image data of a desired nuclear spin in the subject 200. The reconstruction part 10*c* creates mask data in which a distribution of a static magnetic field strength or a distribution of an RF magnetic field strength is reflected with respect to a region having a reconstructed image with reference to a gradient magnetic field map, a static magnetic field map, and an RF magnetic field map stored in the storage part 10*d*.

The storage part 10*d* stores the magnetic resonance signal data, the spectrum data, or the image data for each subject. Additionally, the storage part 10*d* stores the gradient magnetic field map, the static magnetic field map, and the RF magnetic field map.

The gradient magnetic field map is a data table showing a distortion of an actual gradient magnetic field, generated by the gradient magnetic field coil 2, with respect to an ideal gradient magnetic field. The static magnetic field map shows a spatial distribution of the static magnetic field strength. The RF magnetic field map shows a spatial distribution of the REF magnetic field strength.

The display part 10*e* displays a variety of information such as spectrum data or image data under a control of the main control part 10*g*. As the display part 10*e*, a display device such as an LCD display device or the like may be used.

The input part 10*f* receives a variety of instructions or information input from an operator. As the input part 10*f*, a pointing device such as a mouse or a track ball, a selection device such as a mode changing switch, or an input device such as a keyboard may be appropriately used.

The main control part 10*g* includes a CPU, a memory, and the like which are not shown in the drawings, and generally controls the MRI apparatus 100. The main control part 10*g* has a variety of functions described below as well as a control function for realizing known functions in the known MRI apparatus. One of the functions is to input an allowable deviation amount designated by the operator via the input part 10*f*. Another of the functions is to create display data by means of the image data and the mask data obtained by the reconstruction part 10*c*.

The gradient magnetic field map shows a relationship for multiple positions in a space where the gradient magnetic field is formed and shows a physical deviation amount between a coordinate (hereinafter, referred to as "a detected coordinate") obtained from the gradient magnetic field strength for each position and an actual coordinate (hereinafter, referred to as "an actual coordinate") an the corresponding position. The deviation of the detected coordinate with respect to the actual coordinate occurs respectively in the X-axis, Y-axis, and Z-axis directions. That is, the deviation amount is expressed as a vector amount including deviation amounts dx, dy, and dz in the X-axis, Y-axis, and Z-axis directions. However, in this embodiment, since it is necessary to obtain only the deviation magnitude for the detected coordinate with respect to the actual coordinate, the deviation amount may be expressed as a scalar amount.

FIG. 2 is a diagram showing an example of the gradient magnetic field map. This gradient magnetic field map shows a deviation amount for each position from a position P (0, 0, 0) to a position P (32, 32, 32), where the position P (0, 0, 0) denotes a center of a space where the gradient magnetic field is formed. Additionally, a coordinate value is decided by dividing the width in the X-axis, Y-axis, and Z-axis directions as a target of the gradient magnetic field map by the same interval. Specifically, a region of $3.28\times10^7$ mm$^3$ is divided by an interval of 10 mm in the X-axis, Y-axis, and Z-axis directions to thereby obtain the coordinate values up to the coordinate value 32. Then, the deviation amount for each position is expressed by the scalar amount using the unit of mm. For example, at the position P (32, 0, 0), the deviation amount for the detected coordinate with respect to the actual coordinate is 5 mm. Additionally, the range of the coordinate value shown in the gradient magnetic field map may be arbitrarily set. That is, the coordinate value may be expressed as a negative value or a value having a positive value and a negative value. The region indicated by the coordinate value may be smaller or larger than 320 mm$^3$. The interval corresponding to a variation for one coordinate value may be smaller or larger than 10 mm.

For example, the static magnetic field map is obtained in such a manner that static magnetic field uniformity information is obtained as a spherical surface data upon installing the MRI apparatus 100 and is applied to a Le Gendre spherical surface function. It is possible to calculate the uniformity of the magnetic field for each coordinate point in terms of a series expansion using the static magnetic field map data. Alternatively, the static magnetic field map may be a coordinate table showing the static magnetic field strength for each of the X, Y, and Z coordinate positions.

FIG. 3 is a diagram showing an example of the static magnetic field map. This static magnetic field map shows a deviation rate of the static magnetic field strength for each position in the common coordinate system of the gradient magnetic field map. The deviation rate of the static magnetic field strength for each position with respect to a reference value is expressed by the unit of ppm, where the reference value is set by the static magnetic field strength at the static magnetic field center, that is, the position P (0, 0, 0). For example, the deviation rate for the position P (32, 0, 0) with respect to the reference value of the static magnetic field strength is expressed by 3 ppm.

The RF magnetic field map data is obtained by carrying out a calibration using a correction term based on a phantom imaging during an installation on the basis of a uniformity data of a local magnetic field $B_1$ obtained upon designing the sending RF coil 6. Recently, in the MRI apparatus of a high magnetic field type, multiple divisions of a WB transmission are used in some cases. In this case, since a spatial distribution of the RF magnetic field strength is changed by a channel combination, the RF magnetic field map for each combination is prepared.

FIG. 4 is a diagram showing an example of the RF magnetic field map. This RF magnetic field map shows a match rate of the RF magnetic field for each position in the common coordinate system of the gradient magnetic field map. The match rate of the RF magnetic field strength for each position with respect to a reference value is expressed by the unit of %, where the reference value is set by the RF magnetic field strength at the position P (0, 0, 0). For example, the match rate for the position P (32, 0, 0) with respect to the reference value of the RF magnetic field strength is expressed by 70%.

Incidentally, the static magnetic field map and the RF magnetic field map are changed due to the influence of the subject 200. Thus, it is desirable that the static magnetic field map an the RF magnetic field map are created on the basis of the magnetic resonance signal collected in a state where the subject 200 is disposed in the imaging space. However, the static magnetic field map and the RF magnetic field map created without considering the existence of the subject 200 substantially show a distribution of an image quality deterioration degree caused by the nonuniformity of the static magnetic field strength distribution or the nonuniformity of the RF magnetic field strength distribution. Accordingly, the static magnetic field map and the RF magnetic field map created without considering the existence of the subject 200 are prepared in advance as a default static magnetic field map and a default RF magnetic field map, and may be used.

First Embodiment

Next an operation of the MRI apparatus 100 with the above-described configuration according to a first embodiment will be described.

Since an imaging operation for the subject 200 is the same as that of the known MRI apparatus, herein, the detailed description thereof will be omitted.

Figure 5:
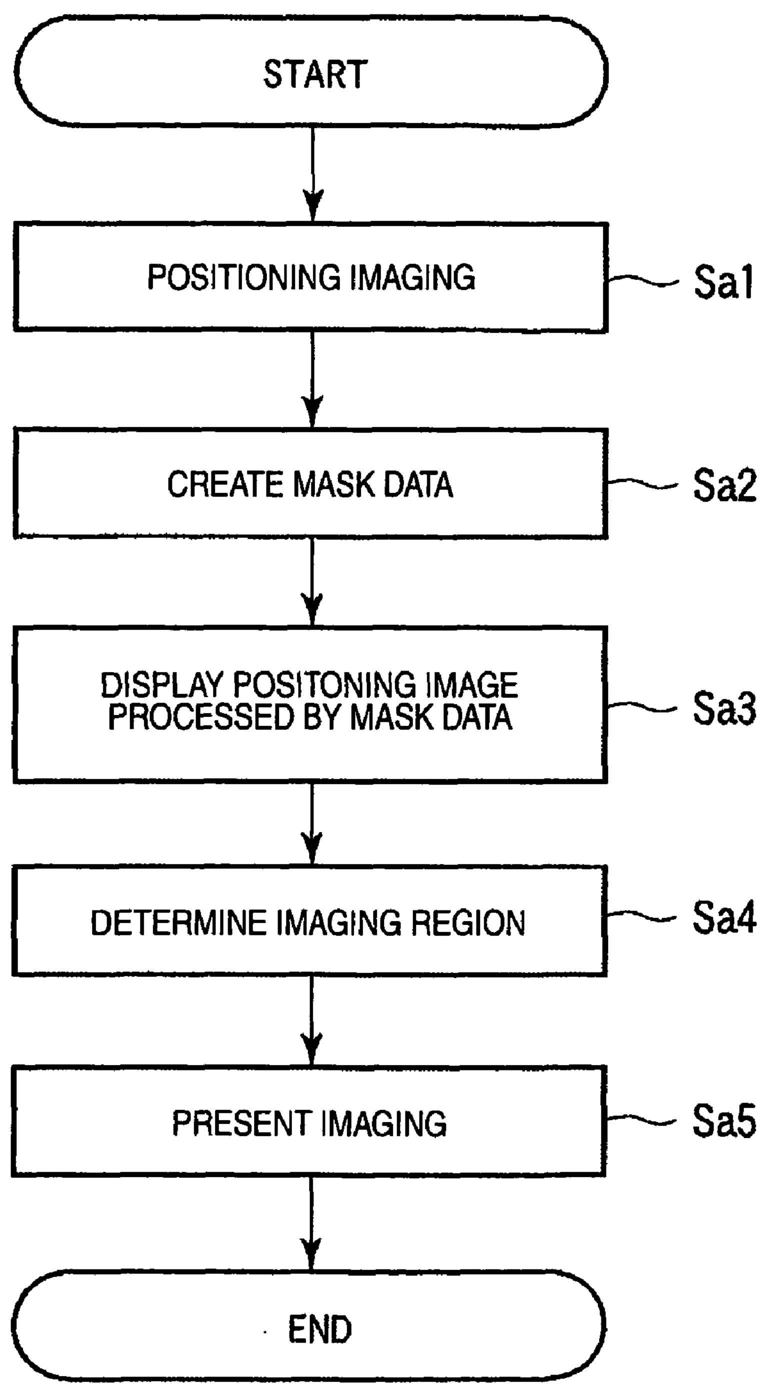
FIG. 5 is a flowchart showing a procedure of a main control part according to a first embodiment.

FIG. 5 is a flowchart showing a procedure of the main control part 10*g* according to the first embodiment.

Before the subject 200 is imaged to obtain a medical diagnostic image, in Step Sa1, the main control part 10*g* controls the respective units so as to image a positioning image.

In Step Sa2, the main control part 10*g* creates mask data. Then, in Step Sa3, the main control part 10*g* displays the positioning image processed by the mask data on the display part 10*e*. Additionally, the detail of the processes in Steps Sa2 and Sa3 will be described below.

In Step Sa4, the main control part 10*g* sets a region used for imaging the medical diagnostic image on the positioning image displayed in Step Sa3 in accordance with an operator's instruction.

In Step Sa5, the main control part 10*g* carries out the imaging for obtaining the medical diagnostic image from the target region set in Step Sa4.

The processes in Steps Sa2 and Sa3 are any one of three processes described below. Additionally, the main control part 10*g* may have a function of carrying out only one of three processes described below or may have a function of carrying out two or three processes which are selectively carried out in accordance with the operator's instruction.

(Display of Image Quality Deterioration State Caused by Nonlinearity of Gradient Magnetic Field)

The display is carried out on the basis of the display data created by the technique disclosed in Japanese Patent No. 2006-157658 (Japanese Patent Application Laid-Open No. 2007-325665) proposed by the present applicant.

That is, the reconstruction part 10*c* obtains the deviation amount for the position included in the imaging region from the gradient magnetic field map. Then, the reconstruction part 10*c* calculates the deviation amount (hereinafter, referred to as "a pixel distortion") for each position of pixels forming a reconstruction image on the basis of the deviation amount obtained for each position. Accordingly, the reconstruction part 10*c* obtains a map data in which one scalar amount shows the deviation amount for each position of the pixels forming the reconstruction image. Then, the reconstruction part 10*c* creates the mask data by performing a binarization process, in which an allowable level (a default value or an operator's designated value) is set to a threshold value, on the map data.

Figure 6:
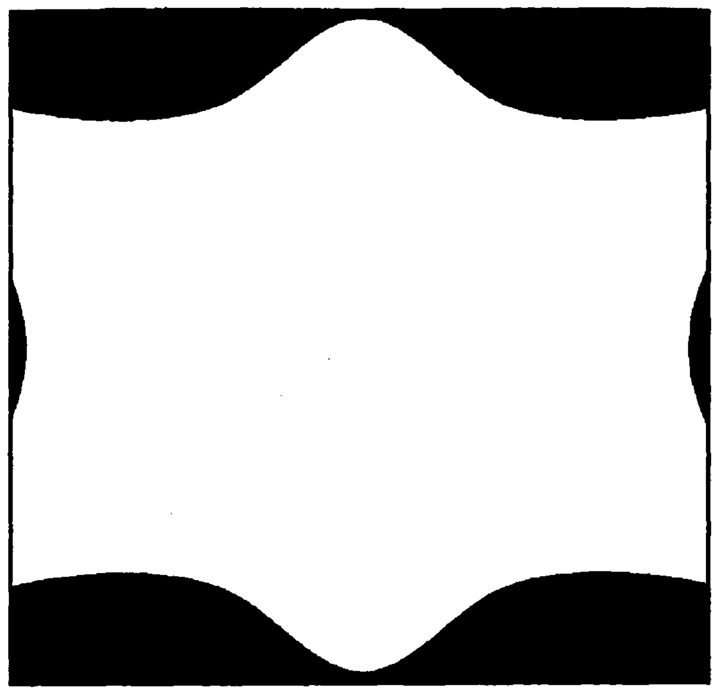
FIG. 6 is a diagram showing an example of an image shown by a mask data.

FIG. 6 is a diagram showing an example of an image shown by the mask data. In this mask data, a black shows a region where the deviation amount is not less than the allowable level.

Figure 7:
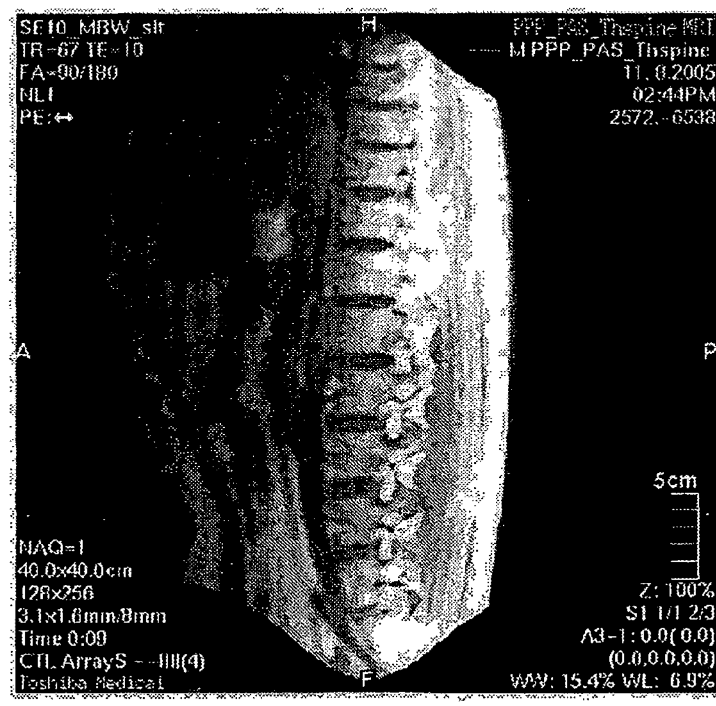
FIG. 7 is a diagram showing an example of an image shown by a display data.
Figure 8:
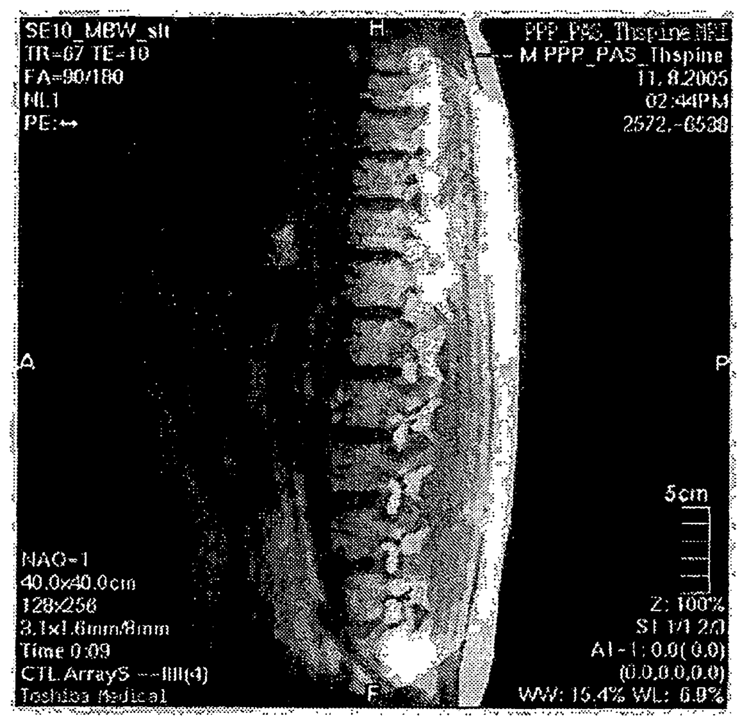
FIG. 8 is a diagram showing an example of the image shown by the display data.

The main control part 10*g* creates the display data by combining the mask data with the data showing the positioning image. At this time, it is possible to create the display data showing, for example, the image shown in FIG. 7 by masking the positioning image with the mask data. Additionally, it is possible to create the display data showing, for example, the image shown in FIG. 8 in such a manner that a pixel value for each pixel is adjusted so that a brightness for each pixel on the positioning image is set to n % and a brightness for each pixel shown by the mask data is set to (100−n) %, and the pixel values for the same pixels of both data are added. Additionally, FIG. 8 shows a case where n is set to "70". In all cases, the brightness for the pixel in the region where the deviation amount is less than the allowable level is 100%. The brightness for the pixel in the region where the deviation amount is not less than the allowable level is reduced to n %. Additionally, in FIGS. 7 and 8, text information showing an imaging condition and the like is displayed while overlapping with the information shown by the mask data and the positioning image.

The above-described image shown by the display data is displayed by the display part 10*e* under the control of the main control part 10*g*.

(Display of Image Quality Deterioration State Caused by Nonuniformity of Static Magnetic Field Strength)

Figure 9:
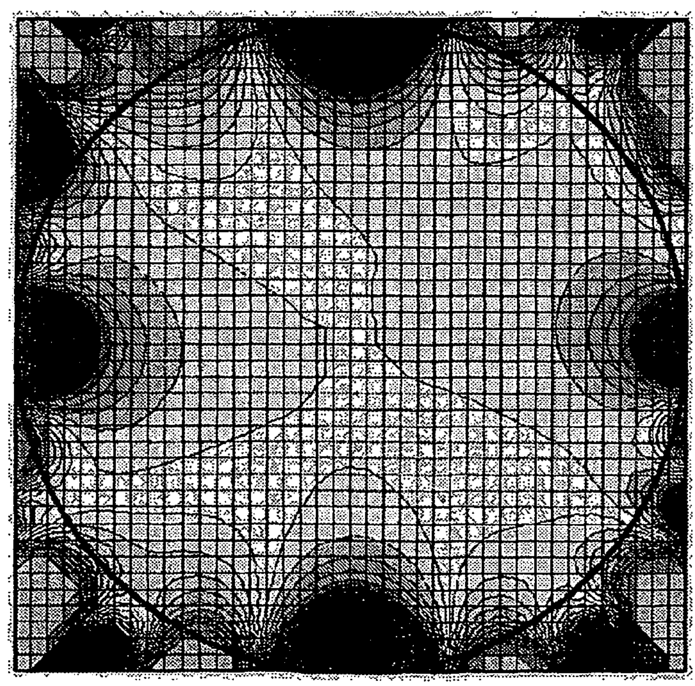
FIG. 9 is a diagram showing an example of the static magnetic field map stored in a storage part shown in FIG. 1.

FIG. 9 is a diagram showing an example of a static magnetic field strength distribution in one section.

The static magnetic field map shows a tendency of the static magnetic field strength distribution. Thus, in the same manner as the case of the gradient magnetic field, the main control part 10*g* basically creates the mask data by performing the binarization process, in which the allowable level (the default value or the operator's designated value) is set to the threshold value, on the static magnetic field map; creates the display data by combining the mask data with the data showing the positioning image; and then carries out the display based on the display data in terms of the display part 10*e*.

Figure 10:
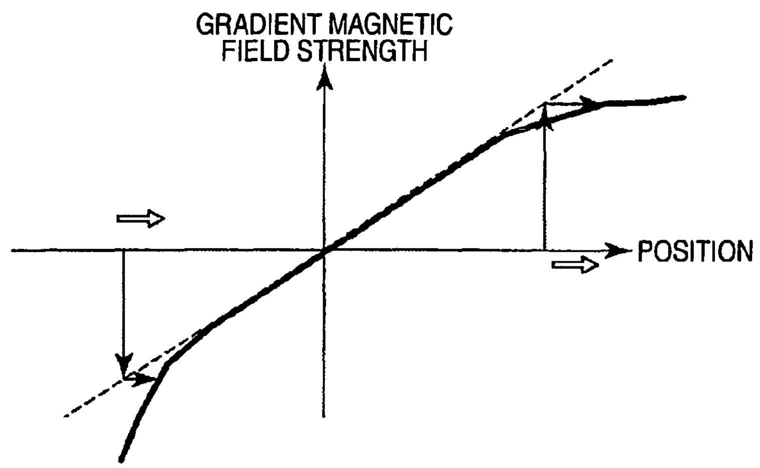
FIG. 10 is a diagram showing an example of a nonlinearity of the gradient magnetic field.
Figure 11:
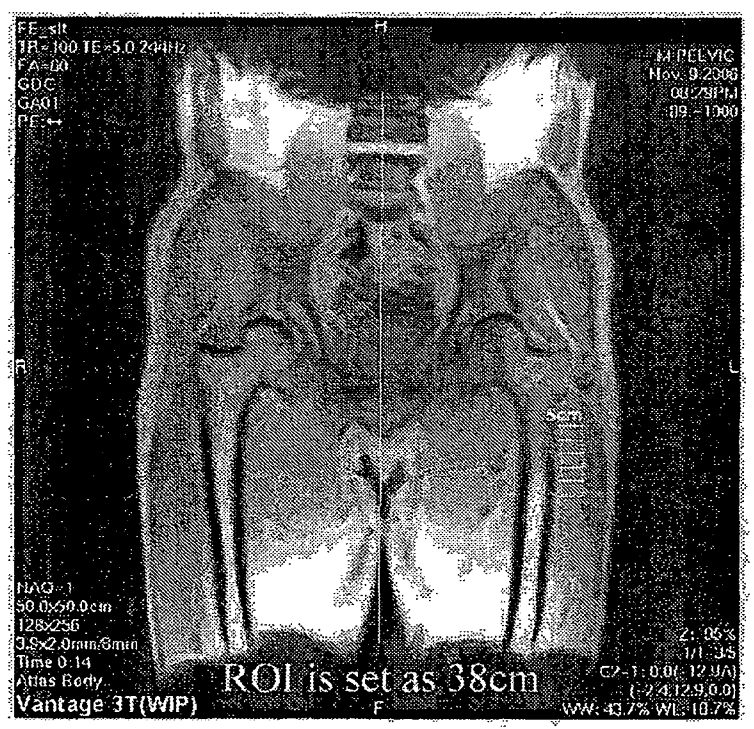
FIG. 11 is a diagram showing an example of an image in which the nonlinearity of the gradient magnetic field is corrected.
Figure 12:
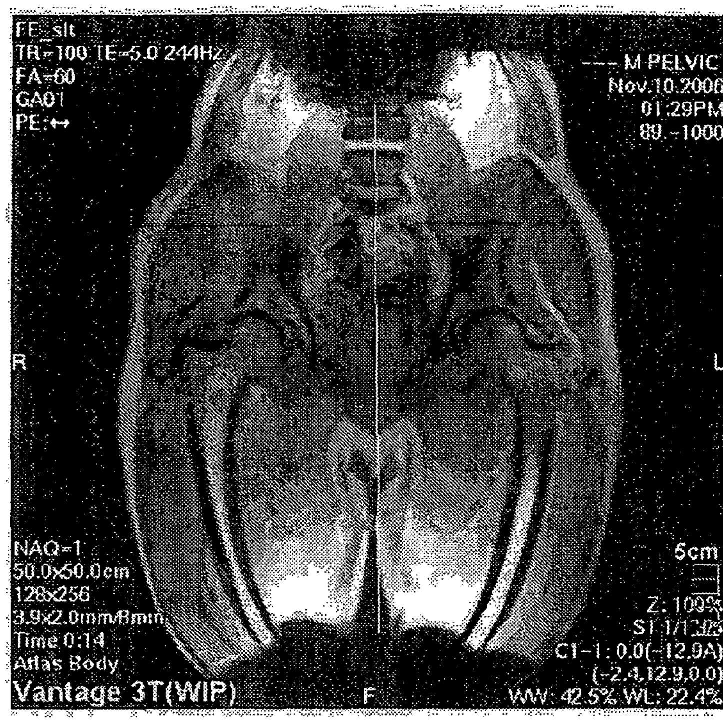
FIG. 12 is a diagram showing an example of a positioning image in which the nonlinearity of the gradient magnetic field is not corrected.

However, the gradient magnetic field has, for example, the nonlinearity shown in FIG. 10, and the nonlinearity of the gradient magnetic field is not reflected in the static magnetic field map shown in FIG. 9. Accordingly, FIG. 9 shows the static magnetic field strength distribution for each position of, for example, the image which is shown in FIG. 11 and in which the nonlinearity of the gradient magnetic field is corrected. Then, for this reason, it is not possible to correctly show the static magnetic field strength distribution of, for example, the image which is shown in FIG. 12 and in which the nonlinearity of the gradient magnetic field is not corrected. Additionally, the positioning image is an image in which the nonlinearity of the gradient magnetic field is not corrected.

Thus, the reconstruction part 10*c* creates the mask data in such a manner that an influence of the nonlinearity of the gradient magnetic field is applied to the static magnetic field map stored in the storage part 10*d* to be distorted, and the same binarization process as that of the gradient magnetic field is performed on the distorted static magnetic field map.

Accordingly, since both the positioning image and the mask data have the distortion caused by the nonlinearity of the gradient magnetic field, it is possible to obtain the display data correctly showing a state where the positioning image is influenced by the nonuniformity of the static magnetic field strength.

Incidentally, in the case of an SE (spin echo) system sequence such as FSE (fast spin echo), the influence of the nonuniformity of the magnetic field is dependent on an ETS (echo interval) or a TE (echo time). That is, as the ETS or TE is long, the signal strength is reduced due to the nonuniformity of the magnetic field. Additionally, the influence of the nonuniformity of the magnetic field is substantially dependent on a slice thickness in the case of a two-dimension (2D) multi slice imaging, and is dependent on a pixel size in the case of a three-dimension (3D) imaging. That is, as the slice thickness of the imaging target is thicker or the pixel size is larger, the signal strength is more reduced due to the nonuniformity of the magnetic field at the pixel. For example, in the uniformities of the magnetic field of 3 ppm, 4 ppm, and 5 ppm, the slice thickness of about 10 mm, 5 mm, and 3 mm are limits respectively corresponding thereto and capable of obtaining the strength necessary for the imaging. In the case of FE (field echo), the uniformity of the magnetic field is further reduced due to the function of TE. For example, in the slice thickness of 5 mm, the magnetic field uniformity limit capable of obtaining the signal strength necessary for the imaging is 3 ppm in the case where the TE is 2.3 ms, but is about 1.5 ppm in the case where the TE is 9 ms.

Additionally, in a readout (RO) direction, a pixel deviation occurs depending on a collection band. That is, in the case where the static magnetic field strength is 1.5 T, the distortion of 1 pixel occurs in correspondence to the nonuniformity of the magnetic field of 1.5 ppm during the collection at the band of 100 Hz/pixel.

Accordingly, it is possible to calculate the pixel distortion amount depending on the imaging band, the slice thickness, and the designated TE. Thus, it is desirable to show a guide of the distortion amount calculated in this manner. Specifically, the mask data may be created in such a manner that a map showing a distortion amount distribution is obtained, and the binarization process is further performed on the map.

When the image distortion state caused by the nonuniformity of the static magnetic field strength is displayed while overlapping with the positioning image in this manner, the operator is capable of easily and reliably setting the imaging position by avoiding the region having the large distortion. Alternatively, when the operator changes the imaging parameter while checking the display image, it is possible to find out the imaging parameter in which the imaging position is a region having the small distortion.

(Display of Image Quality Deterioration State Caused by Nonuniformity of RF Magnetic Field)

Figure 13:
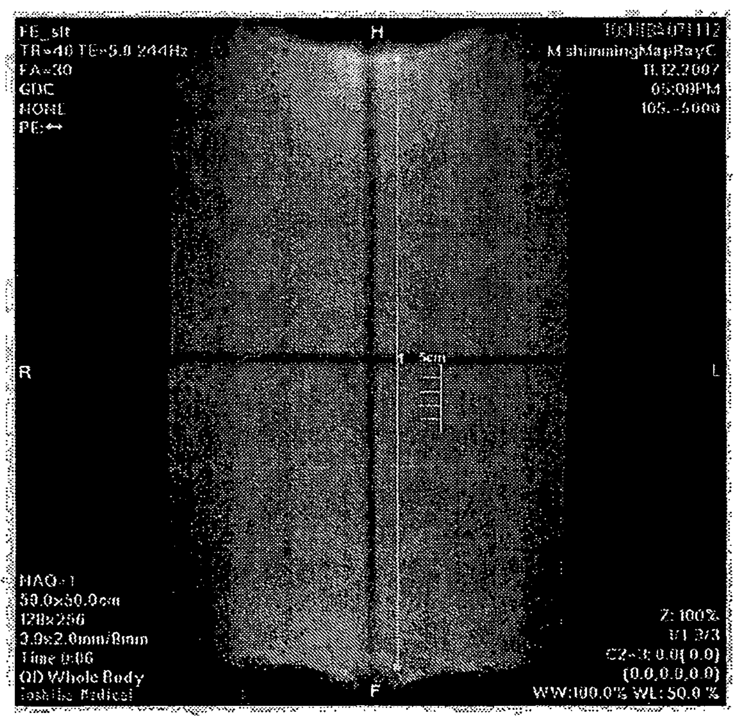
FIG. 13 is a diagram showing an example of an image obtained by imaging a phantom for a calibration upon installing the MRI apparatus.

FIG. 13 is a diagram showing an example of the image obtained by imaging a phantom for a calibration upon installing the MRI apparatus 100. Upon imaging the image shown in FIG. 13, the correction of the nonlinearity of the gradient magnetic field is carried out.

Figure 14:
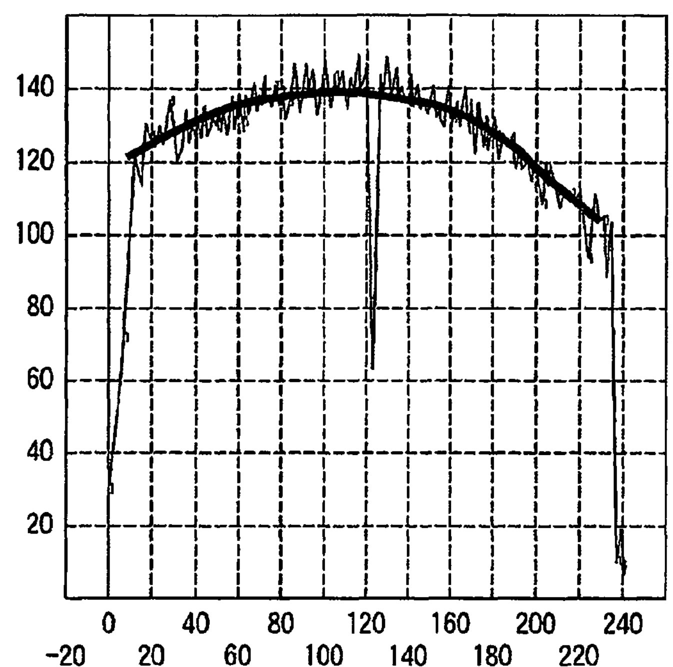
FIG. 14 is a diagram showing a Z-axis-direction brightness distribution at a certain position of the image shown in FIG. 13 and an RF magnetic field strength distribution obtained on the basis of the brightness distribution.

FIG. 14 is a diagram showing a Z-axis-direction brightness distribution at a certain position of the image shown in FIG. 13 and an REF magnetic field strength distribution obtained on the basis of the brightness distribution. In FIG. 14, the brightness distribution is depicted by the small bent line. A low-frequency variation of the brightness distribution variation is mainly caused by the nonuniformity of the RF magnetic field. For this reason, the RF magnetic field strength distribution is obtained on the basis of the brightness distribution shown in FIG. 13 and is depicted by the gentle curve shown in FIG. 13. Then, the RF magnetic field map stored in the storage part 10*d* together with the RF magnetic field strength distribution obtained as above is created.

Then, in the same manner as the case of the gradient magnetic field, the main control part 10*g* basically creates the mask data by performing the binarization process, in which the allowable level (the default value or the operator's designated value) is set to the threshold value, on the RF magnetic field map; creates the display data by combining the mask data with the data showing the positioning image; and then carries out the display based on the display data in terms of the display part 10*e*.

However, in the RF magnetic field map, the influence of the nonlinearity of the gradient magnetic field strength is corrected as above. Accordingly, in the RF magnetic field map shown in FIG. 14, the static magnetic field strength distribution for each position of, for example, the image, which is shown in FIG. 12 and in which the nonlinearity of the gradient magnetic field is not corrected, is not correctly shown.

Figure 15:
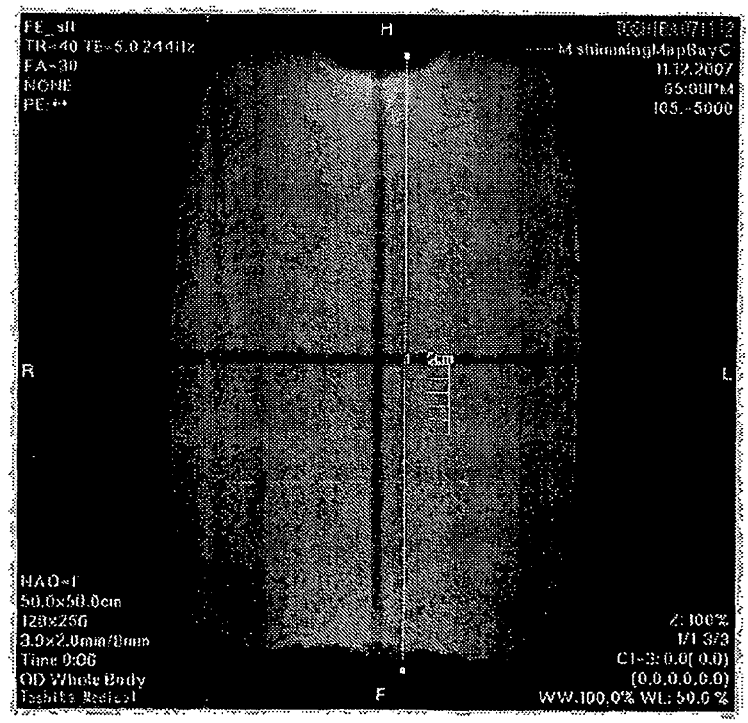
FIG. 15 is a diagram showing an example of an image obtained by imaging the phantom without correcting the nonlinearity of the gradient magnetic field.
Figure 16:
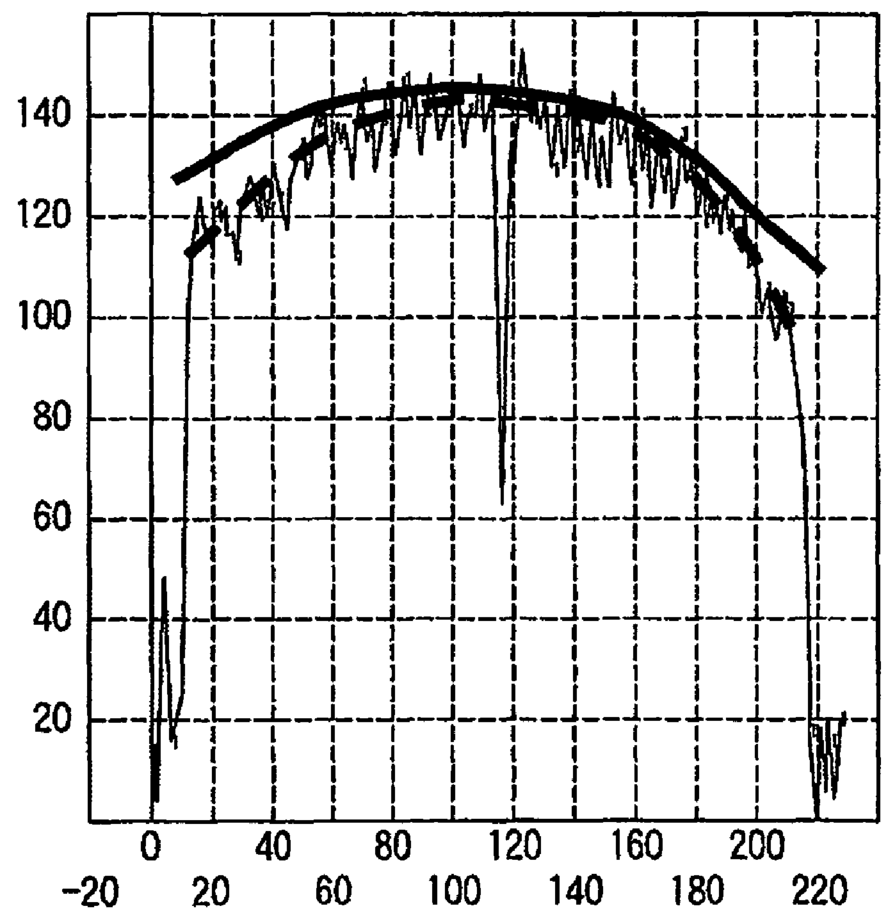
FIG. 16 is a diagram showing a Z-axis-direction brightness distribution at a certain position of the image shown in FIG. 15 and the RF magnetic field map obtained on the basis of the brightness distribution.

FIG. 15 is a diagram showing an example of an image obtained by imaging the phantom without correcting the nonlinearity of the gradient magnetic field. FIG. 16 is a diagram showing a Z-axis-direction brightness distribution at a certain position of the image shown in FIG. 15 and the RF magnetic field map obtained on the basis of the brightness distribution.

In FIG. 16, the gentle curve depicted by the dashed line indicates the RF magnetic field strength distribution obtained on the basis of the brightness distribution depicted by the small bent curve shown in FIG. 16. Additionally, in FIG. 16, the gentle curve depicted by the solid line indicates the strength distribution reflected in the RF magnetic field map. For this reason, the RF magnetic field map stored in the storage part 10*d* is different from the RF magnetic field strength distribution without the correction of the nonlinearity of the gradient magnetic field.

Thus, the reconstruction part 10*c* creates the mask data in such a manner that the influence of the nonlinearity of the gradient magnetic field is removed from the RF magnetic field map stored in the storage part 10*d*, and the same binarization process as that of the gradient magnetic field is carried out.

Accordingly, since both the positioning image and the mask data have the distortion caused by the nonlinearity of the gradient magnetic field, it is possible to obtain the display data correctly showing a state where the positioning image is influenced by the nonuniformity of the RF magnetic field strength.

Incidentally, the influence of the nonuniformity of the RF magnetic field is small in an EASE (fast advanced spin echo) and a T2 emphasis (T2W) of a FSE capable of utilizing the condition of a FE and a CPMG (Carr-Purcell-Meiboom-Gill) of a low flip angle, and it is supposed that an attenuation of about 30 to 40% corresponding to an PA (flip angle) is substantially an allowable range. In an SE in which an SNR (signal to noise ratio) is dependent on the pulse of 180°, a signal value is hardly influenced by a variation of about 10 to 20%. Meanwhile, an IR (inversion recovery) pulse and a fat suppression (Fatsat) pulse are largely influenced by the nonuniformity, and the influence is large since the suppression of the fat signal is nonuniform within an error of 10%. The RF magnetic field distribution is changed in accordance with the subject 200.

For this reason, it is desirable that the threshold value applied upon generating the mask data is appropriately set in consideration of the above-described circumstance. Thus, for example, it is convenient that a database having the threshold value set in correspondence to a weight and an imaging portion is stored in the storage part 10*d*, and the appropriate threshold value is automatically set by the main control part 10*g* in accordance with the weight and the imaging portion of the subject 200. Alternatively, a range of a threshold value candidate stored in the database may be stored, and an arbitrary threshold value within the range may be selected by the operator for an application.

Specifically, regarding a head imaging, it is possible to carry out the imaging at the center of the magnetic field. Additionally, the imaging region is narrow, but the Z-direction uniformity distribution occurs. Accordingly, it is efficient to show a valid range of a Z-direction fat suppression pulse and the like (in this narrow region, the influence is not substantially dependent on the distortion correction).

Alternatively, in the case of a large-region Imaging such as an abdominal imaging, a problem arises in the nonuniformity of the RF magnetic field strength distribution in a Z direction. That is, at an off center of Z=200 mm, the RF magnetic field is dependent on a physique of the subject 200, and the nonuniformity of the RF magnetic field increases up to an unignorable level. That is, amplitude attenuation is about 30%, and the RF magnetic field is influenced by a signal reduction even in the FE and FSE. Then, since the influence range is considerable in a fat suppression pulse or an IR pulse, a suppression irregularity and the like are supposed as a coronal section easily recognizable in the imaging section. That is, in accordance with an imaging sequence or an imaging condition (whether the IR pulse is used or the fat suppression pulse is used), a range in which a sensitivity irregularity or a suppression irregularity does not occur is displayed on a plane of the coronal section. In the case where the fat suppression pulse is used, a region capable of obtaining a uniform fat suppression is displayed as, for example, a region having the nonuniformity of 10% or less. Alternatively, a region, in which the IR pulse is uniformly added, may be displayed as a region having the nonuniformity of 20% or less by changing the brightness thereof in the same manner as the linearity of the gradient magnetic field.

In the case of the FE and FSE, since it is possible to carry out the imaging in a region having the nonuniformity of 40% or less, the region range is displayed.

When the brightness irregularity state caused by the nonuniformity of the RF magnetic field strength is displayed while overlapping with the positioning image in this manner, the operator is capable of easily and reliably setting the imaging position by avoiding the region having the large brightness irregularity. Alternatively, when the operator changes the imaging parameter while checking the display image, it is possible to find out the imaging parameter in which the imaging position is a region having the small brightness irregularity.

Second Embodiment

Next, an operation of the MRI apparatus 100 according to a second embodiment of the invention will be described.

Figure 17:
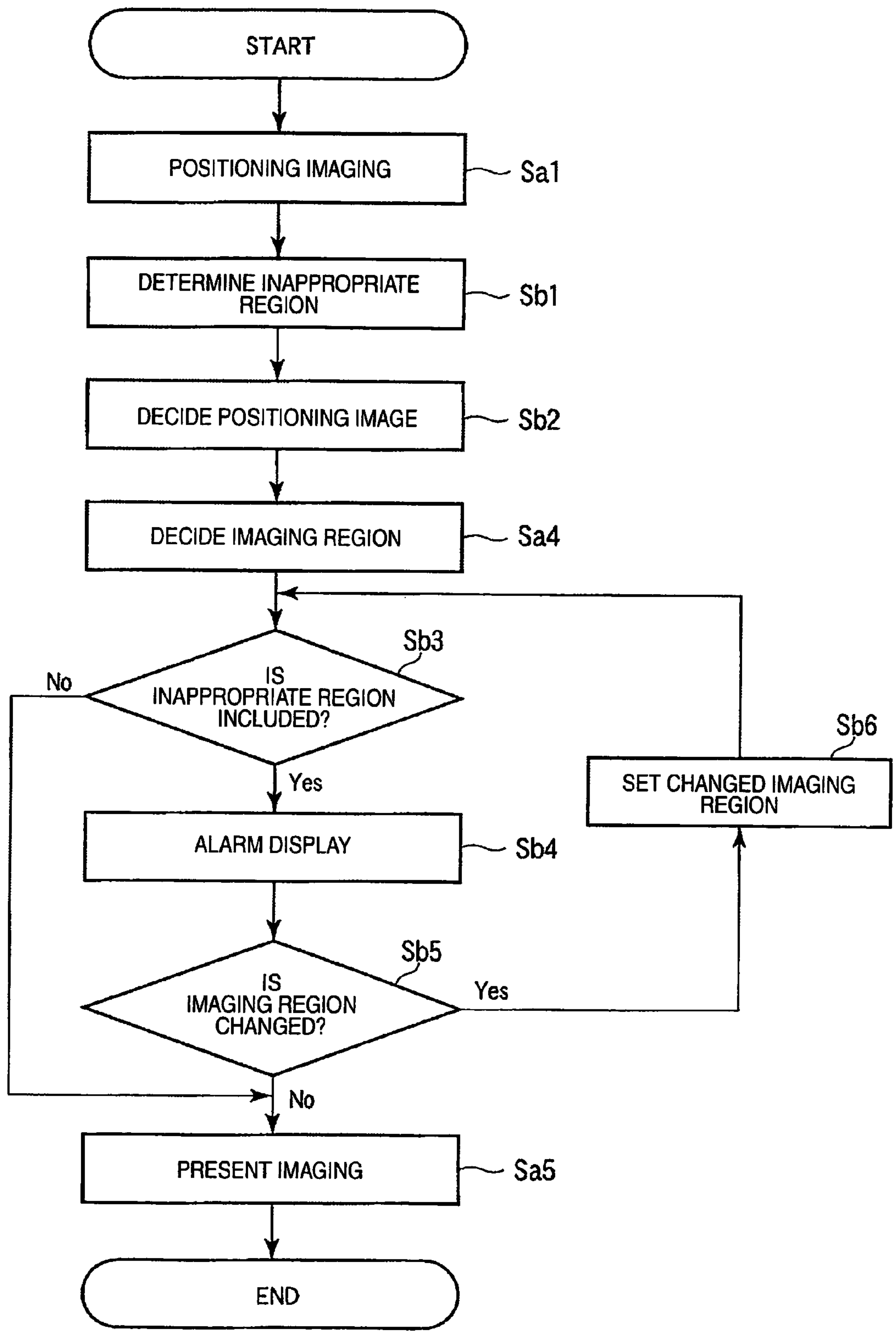
FIG. 17 is a flowchart showing a procedure of a main control part according to a second embodiment.

FIG. 17 is a flowchart showing a procedure of the main control part 10*g* according to the second embodiment. Additionally, the same reference numerals are given to the steps performing the same processes as those of FIG. 5, and the detailed description thereof will be omitted.

In Step Sa1, after the positioning image is imaged, the main control part 10*g* moves the current process to Step Sb1. In Step Sb1, the main control part 10*g* determines a region which is not appropriate for imaging the medical diagnostic image (hereinafter, referred to as "an inappropriate region). It is possible to determine the inappropriate region, for example, as a region not more than the threshold value of the mask data according to the first embodiment.

In Step Sb2, the main control part 10*g* displays the positioning image obtained in Step Sa1 on the display part 10*e* without carrying out the same process as that of the first embodiment. Then, the main control cart 10*g* allows the operator to designate a region for imaging the medical diagnostic image on the positioning images. Thus, in Step Sa4, the main control part 10*g* sets the imaging region in accordance with the operator's instruction. At this time, the operator designates the imaging region without checking any of the image quality deterioration state caused by the nonuniformity of the RF magnetic field, the nonuniformity of the static magnetic field, or the nonlinearity of the gradient magnetic field. For this reason, the imaging region may be set together with the inappropriate region.

Thus, in Step Sb3, the main control part 10*g* determines whether the imaging region set in Step Sa4 includes the inappropriate region. Then, when the imaging region includes the inappropriate region, the main control part 10*g* moves the current process from Step Sb3 to Step Sb4.

In Step Sb4, the main control part 10*g* makes the display part 10*e* generate an alarm display in order to inform the operator of the fact that the imaging region includes the inappropriate region. The content of the alarm display may be arbitrarily set, but for example, any one of the following alarm displays may be supposed.

(1) The operator is simply informed of the fact that the imaging region includes the inappropriate region.

(2) The operator is informed of which portion out of the imaging region overlaps with the inappropriate region.

(3) The operator is advised to carry out the imaging in such a manner that the portion of the imaging region not overlapping with the inappropriate region is first imaged, and the portion or the imaging region overlapping with the inappropriate region is imaged after changing the condition.

In Step Sb5, the main control part 10*g* checks whether the operator requires the change of the imaging region. Then, when the change of the imaging region is required, the main control part 10*g* moves the current process from Step Sb5 to Step Sb6.

In Step Sb6, the main control part 10*g* sets the changed imaging region. The changed imaging region may be set in accordance with the operator's instruction or may be automatically set by the main control part 10*g* so that the inappropriate region is excluded. Then, when the changed imaging region is completed to be set, the main control part 10*g* repeats the process of Step Sb3 and thereafter.

When it is checked that the imaging region does not include the inappropriate region in Step Sb3 or when it is checked that the change of the imaging region is not required by the operator in Step Sb5, the main control part 10*g* moves the current process to Step Sa5. Then, in Step Sa5, the main control part 10*g* controls the respective units so as to carry out the present imaging in a state where the imaging region set at this time point is set to a target.

As described above, according to the embodiment, the operator is capable of designating the imaging region without recognizing any of the image quality deterioration state caused by the nonuniformity of the RF magnetic field, the nonuniformity of the static magnetic field strength, or the nonlinearity of the gradient magnetic field. Then, in the case where the designated imaging region includes a region possibly causing the image quality deterioration of which a degree exceeds the allowable level, it is possible to allow the operator to recognize the case by means of the alarm display.

This embodiment may be modified into various forms as below.

(1) The reconstruction part 10*c* may use a value arbitrarily designated by the operator as the threshold value applied upon creating the mask data showing the range of the image quality deterioration caused by the nonuniformity of the RF magnetic field or the static magnetic field strength. Specifically, it may be supposed that the reconstruction part 10*c* uses the threshold value in accordance with the parameter set in advance for a distortion amount or a signal reduction amount which is allowed to designate a precision guarantee range of the MRI apparatus 100. Additionally, the brightness of the mask data upon combining the positioning image with the mask data showing the range of the image quality deterioration caused by the nonuniformity of the RF magnetic field or the static magnetic field strength may be changed in the same manner as the case of the mask data showing the range of the image quality deterioration caused by the nonlinearity of the gradient magnetic field. Specifically, in consideration of the distortion (includes a determination of these directions of the frequency encode and the phase encode) caused by the uniformity of the magnetic field and the distortion caused by the gradient magnetic field as the image quality deterioration degree, for example, the position precision of 3 mm, is set with respect to the distortion caused by the linearity of the magnetic field, and in a portion having the larger distortion on the positioning image, the pixel brightness is reduced by, for example, 50%. Accordingly, it is possible to display a boundary region of a hairline shape and to obtain information on a region having the larger distortion.

(2) The image quality deterioration may be displayed by overlapping the nonuniformity of the static magnetic field with the nonuniformity of the RF magnetic field.

As the clinical viewpoint influenced by the nonuniformity of the static magnetic field and the nonuniformity of the RF magnetic field, for example, a fat suppression may be supposed. In the case of the fat suppression, the uniformity of the RF magnetic field is required to have higher precision than that of a general imaging signal reduction amount. For example, instead of a signal reduction region having the nonuniformity of 10% or less, a contrast insufficient region is displayed on the positioning image, and the imaging position is desirably decided in the range. Regarding the nonuniformity of the static magnetic field, since a range in which the fat suppression irregularity is displayed requires to have higher precision than a range in which a signal reduction is caused by a signal offset in a pixel due to the nonuniformity of the magnetic field in a general FE and the like, a fat suppression insufficient region is displayed on the positioning image in the same manner, and the imaging position is desirably decided in the range. As a result, the image quality deterioration range is displayed in the form of AND regions of the two regions.

Meanwhile, in an imaging method such as an ASL (arterial spin labeling) method in which the requirement for the RF uniformity is strict, but the FFE and the like of the readout part is not particularly and largely influenced by the nonuniformity of the static magnetic field, it is possible to show the recommended imaging region using only the uniformity of the RF magnetic field.

On the contrary, in a single-shot EPI method, the requirement for the uniformity of the RF magnetic field is not strict, but the requirement for the uniformity of the static magnetic field is strict due to the image distortion.

In an actual operation, it is desirable that the imaging region is displayed in consideration of a free pulse such as the fat suppression or the imaging influenced by both the uniformity influence. Additionally, since the uniformity influence degree is changed in accordance with an RF excitation pulse band, a data collection time, a TE, a slice thickness, and the like, it is desirable that the uniformity influence degree is automatically recalculated whenever the parameters are updated. In the case where a cost of the recalculation is high, the recalculation may be carried out by pressing a refresh button as a trigger.

(3) As the region, the image quality deterioration display may be carried out.

Regarding the positioning section, a plurality of sections such as a perpendicular section between a coronal and an axial or a section parallel to the axial is used. When a region display is performed thereon, it is possible to display a substantially three-dimensional uniform region.

(4) The mask data may be created in such a manner that the influence of the nonlinearity of the gradient magnetic field is applied to the static magnetic field map to be distorted, the distorted static magnetic field map is stored in the storage part 10*d*, and then the binarization process is performed on the static magnetic field map stored in the storage part 10*d*.

(5) The mask data may be created in such a manner that the storage part 10*d* stores the distorted static magnetic field map obtained by applying the influence of the nonlinearity of the gradient magnetic field thereto, and the binarization process is performed on the distorted static magnetic field map.

(6) The mask data may be created in such a manner that the storage part 10*d* stores the RF magnetic field map obtained by removing the influence of the nonlinearity of the gradient magnetic field or the RF magnetic field map created together with the RF magnetic field strength distribution obtained by imaging the phantom without correcting the non linearity of the gradient magnetic field, and the binarization process is performed thereon.

(7) A static magnetic field generator may include a corrector such as an iron core or a correcting coil as well as the static magnetic field magnet 1.

(8) Regarding the region having the distortion not less than the allowable level, the image may be different from the region having the distortion less than the allowable level or only the boundary line may overlap by changing a display parameter type, a display color, or chrome in addition to the change of the brightness.

(9) The change of the brightness for the region having the distortion not less than the allowable level may be displayed in gradation in such a manner that the brightness is changed as the distance becomes longer from the boundary of the region having the distortion less than the allowable level. This is a method in which a plurality of allowable values for the distortion degree is provided, and the allowable degree of the image distortion is gradually displayed by applying ratios of n1, n2, and the like thereto. In other words, when the allowable value of 2 mm is set to 90%, the allowable value of 3 mm is set to 80%, the allowable value of 5 mm is set to 70%, and then the allowable value of 10 mm is set to 50%, it is possible to display the distortion degree in gradation.

(10) The positioning may be prohibited in the region having the distortion not less than the allowable level.

(11) Both the positioning image display according to the first embodiment and the alarm display according to the second embodiment may be carried out.

(12) As a specific method of avoiding the inappropriate region according to the second embodiment, a degree of freedom movable between the imaging protocols in a craniocaudal direction of the bed is used. That is, the imaging may be carried out in a uniform range by appropriately moving the bed in a craniocaudal direction for the imaging in the vicinity of the center where the linearity of the gradient magnetic field, the uniformity of the static magnetic field, and the uniformity of the RF magnetic field are excellent.

In the case where the method is developed for a so-called broad-region imaging so that the imaging is carried out in the body region by moving the bed by a predetermined amount and repeating the imaging of a plurality of protocols. However, in the plurality of protocols used at this time, the allowable range is set by the protocols and the whole allowable range is set by the strictest protocol, an expansion may be considered in which the reasonable bed movement amount is decided upon carrying out the imaging by sequentially moving the bed.

Additionally, the present invention is not limited to the above-described embodiments, but the components may be modified in the scope without departing from the gist of the invention. Additionally, various inventions may be made through the appropriate combination of the plurality of components disclosed in the above-described embodiments. For example, several components may be omitted from all the components shown in the above-described embodiments. Then, the components shown in the different embodiments may be appropriately combined.

What is claimed is:

1. A magnetic resonance imaging apparatus comprising:

a generation unit configured to generate a magnetic field;

a reconstruction unit configured to reconstruct an image for a subject on the basis of a magnetic resonance signal radiated from the subject in the magnetic field;

a presumption unit configured to presume a distribution of an image quality deterioration degree occurring in the image on the basis of a precision at which the generation unit generates the magnetic field; and a creation unit configured to create a display image showing the distribution of the image quality deterioration degree on the image.

2. The magnetic resonance imaging apparatus according to claim 1, wherein the generation unit includes:

a static magnetic field generating section configured to generate a static magnetic field, a gradient magnetic field generating section configured to generate a gradient magnetic field used to overlap with the static magnetic field; and a high-frequency magnetic field generating section configured to generate a high-frequency magnetic field applied to the subject placed in the static magnetic field overlapping with the gradient magnetic field, and wherein the reconstruction unit creates a positioning image for the subject on the basis of the magnetic resonance signal radiated from the subject without correcting a distortion caused by a nonlinearity of the gradient magnetic field, wherein the presumption unit presumes the distribution of the image quality deterioration degree occurring in the positioning image due to a deviation of a static magnetic field strength on the basis of the distortion occurring in the positioning image due to the nonlinearity of the gradient magnetic field and a spatial distribution of the static magnetic field strength, and wherein the creation unit creates a display image showing the distribution of the image quality deterioration degree on the positioning image.

3. The magnetic resonance imaging apparatus according to claim 2, further comprising:

a storage unit configured to store a static magnetic field map showing the spatial distribution of the static magnetic field strength, wherein the presumption unit presumes the distribution of the image quality deterioration degree on the basis of the static magnetic field map having a distortion, the static magnetic field map being distorted in accordance with the distortion occurring in the positioning image due to the nonlinearity of the gradient magnetic field.

4. The magnetic resonance imaging apparatus according to claim 2, further comprising:

a storage unit configured to store a static magnetic field map in which a static magnetic field map showing the spatial distribution of the static magnetic field strength is distorted in accordance with the distortion occurring in the positioning image due to the nonlinearity of the gradient magnetic field, wherein the presumption unit presumes the distribution of the image quality deterioration degree on the basis of the static magnetic field map having the distortion.

5. The magnetic resonance imaging apparatus according to claim 3, wherein the presumption unit creates a mask data showing the image quality deterioration degree as a binary value by performing a binarization process on the static magnetic field map having the distortion, and wherein the creation unit creates the display image by combining the mask data with the positioning image.

6. The magnetic resonance imaging apparatus according to claim 3, wherein the presumption unit creates a distortion amount map showing a spatial distribution of a pixel distortion amount in an imaging condition set on the basis of the spatial distribution of the static magnetic field strength shown in the static magnetic field map having the distortion, and further creates a mask data showing the image quality deterioration degree as a binary value by performing a binarization process on the distortion amount map, and wherein the creation unit creates the display image by combining the mask data with the positioning image.

7. The magnetic resonance imaging apparatus according to claim 5, wherein the presumption unit sets a threshold value for the binarization process to a value designated by the operator.

8. The magnetic resonance imaging apparatus according to claim 2, wherein the creation unit creates the display image by partially changing at least one of brightness and chroma of the positioning image in accordance with the distribution of the image quality deterioration degree.

9. The magnetic resonance imaging apparatus according to claim 1, wherein the generation unit includes:

a static magnetic field generating section configured to generate a static magnetic field, a gradient magnetic field generating section configured to generate a gradient magnetic field used to overlap with the static magnetic field; and a high-frequency magnetic field generating section configured to generate a high-frequency magnetic field applied to the subject placed in the static magnetic field overlapping with the gradient magnetic field, and wherein the magnetic resonance imaging apparatus further comprises a storage unit configured to store a high-frequency magnetic field map including an influence of the nonlinearity of the gradient magnetic field and showing a distribution of a high-frequency magnetic field strength, wherein the reconstruction unit creates a positioning image for the subject on the basis of the magnetic resonance signal radiated from the subject without correcting a distortion caused by the nonlinearity of the gradient magnetic field, wherein the presumption unit presumes the distribution of the image quality deterioration degree occurring in the positioning image due to a deviation of the high-frequency magnetic field strength by removing the influence of the nonlinearity of the gradient magnetic field from the high-frequency magnetic field map, and wherein the creation unit creates a display image showing the distribution of the image quality deterioration degree on the positioning image.

10. The magnetic resonance imaging apparatus according to claim 9, wherein the presumption unit creates a mask data showing the image quality deterioration degree as a binary value by performing a binarization process on the high-frequency magnetic field map in which the influence of the nonlinearity of the gradient magnetic field is removed, and wherein the creation unit creates the display image by combining the mask data with the positioning image.

11. The magnetic resonance imaging apparatus according to claim 10, wherein the presumption unit sets a threshold value for the binarization process to a value designated by the operator.

12. The magnetic resonance imaging apparatus according to claim 10, wherein the presumption unit sets a threshold value for the binarization process to a value in accordance with an imaging condition.

13. The magnetic resonance imaging apparatus according to claim 9, wherein the creation unit creates the display image by partially changing at least one of brightness and chroma of the positioning image in accordance with the distribution of the image quality deterioration degree.

14. The magnetic resonance imaging apparatus according to claim 1, wherein the generation unit includes:

a static magnetic field generating section configured to generate a static magnetic field, a gradient magnetic field generating section configured to generate a gradient magnetic field used to overlap with the static magnetic field; and a high-frequency magnetic field generating section configured to generate a high-frequency magnetic field applied to the subject placed in the static magnetic field overlapping with the gradient magnetic field, and wherein the magnetic resonance imaging apparatus further comprises a storage unit configured to store a high-frequency magnetic field map including an influence of the nonlinearity of the gradient magnetic field and showing a distribution of a high-frequency magnetic field strength, wherein the reconstruction unit creates a positioning image for the subject on the basis of the magnetic resonance signal radiated from the subject without correcting a distortion caused by the nonlinearity of the gradient magnetic field, wherein the presumption unit presumes a distribution of a first image quality deterioration degree occurring in the positioning image due to a deviation of a static magnetic field strength on the basis of the distortion occurring in the positioning image due to the nonlinearity of the gradient magnetic field and a spatial distribution of the static magnetic field strength, and presumes a distribution of a second image quality deterioration degree occurring in the positioning image due to a deviation of the high-frequency magnetic field strength by removing the influence of the nonlinearity of the gradient magnetic field from the high-frequency magnetic field map, and wherein the displaying unit creates the display image showing the distribution of the first image quality deterioration degree and the distribution of the second image quality deterioration degree on the positioning image.

15. The magnetic resonance imaging apparatus according to claim 14, further comprising:

a storage unit configured to store a static magnetic field map showing the spatial distribution of the static magnetic field strength, wherein the presumption unit creates a first mask data showing the first image quality deterioration degree as a binary value by performing a binarization process on the static magnetic field map having a distortion, the static magnetic field map being distorted in accordance with the distortion occurring in the positioning image due to the nonlinearity of the gradient magnetic field, wherein the presumption unit creates a second mask data showing the second image quality deterioration degree as a binary value by performing a binarization process on the high-frequency magnetic field map in which the influence of the nonlinearity of the gradient magnetic field is removed, wherein the creation unit creates the display image by combining the first and second mask data with the positioning image.

16. The magnetic resonance imaging apparatus according to claim 15, further comprising:

a setting unit configured to independently set a first threshold value used for the binarization process for creating the first mask data and a second threshold value used for the binarization process for creating the second mask data.

17. A magnetic resonance imaging apparatus comprising:

a generation unit configured to generate a magnetic field;

a presumption unit configured to presume a distribution of an image quality deterioration degree occurring in an image on the basis of a precision at which the generation unit generates the magnetic field;

a determination unit configured to determine an inappropriate region having an image quality deterioration of which a degree exceeds an allowable level on the basis of the distribution of the image quality deterioration degree;

a setting unit configured to set an imaging region, which is a target for reconstructing a medical diagnostic image for a subject, in accordance with an operator's instruction;

an information unit configured to inform the operator of a fact that the imaging region includes the inappropriate region; and a reconstruction unit configured to reconstruct an image for the subject on the imaging region on the basis of a magnetic resonance signal radiated from the subject in the magnetic field.

18. A magnetic resonance imaging method comprising the steps of:

generating a magnetic field;

presuming a distribution of an image quality deterioration degree occurring in an image on the basis of a precision at which the generation unit generates the magnetic field;

determining an inappropriate region having an image quality deterioration of which a degree exceeds an allowable level on the basis of the distribution of the image quality deterioration degree;

setting an imaging region, which is a target for reconstructing a medical diagnostic image for a subject, in accordance with an operator's instruction;

informing the operator of a fact that the imaging region includes the inappropriate region; and reconstructing an image for the subject on the imaging region on the basis of a magnetic resonance signal radiated from the subject in the magnetic field.

* * * * *